United States Patent [19]

Schulenberg

[11] 4,150,134
[45] Apr. 17, 1979

[54] AMINOALKOXY SUBSTITUTED 9(ARYL OR ARALKYL)-ACRIDINES

[75] Inventor: John W. Schulenberg, Delmar, N.Y.

[73] Assignee: Sterling Drug Inc., New York, N.Y.

[21] Appl. No.: 774,399

[22] Filed: Mar. 4, 1977

Related U.S. Application Data

[63] Continuation-in-part of Ser. No. 677,772, Apr. 16, 1976, abandoned.

[51] Int. Cl.$^2$ .................. A61K 31/47; C07D 219/06
[52] U.S. Cl. .................. 424/257; 424/248.56; 424/250; 546/103
[58] Field of Search .................. 260/279 R, 268 TR; 544/80, 126, 361; 424/250, 257, 248.56

[56] References Cited

U.S. PATENT DOCUMENTS

| | | | |
|---|---|---|---|
| 1,727,480 | 9/1929 | Mietzsch | 260/279 R |
| 2,645,594 | 7/1953 | Tabern | 260/279 R X |
| 2,732,373 | 1/1956 | Steiger | 260/279 R |
| 2,732,374 | 1/1956 | Steiger | 260/279 R |
| 3,131,190 | 4/1964 | Zirkle | 260/279 R |
| 3,131,191 | 4/1964 | Douglas et al. | 260/286 R |
| 3,331,849 | 7/1967 | Shavel, Jr. et al. | 260/286 Q |
| 3,597,430 | 8/1971 | Kaiser et al. | 260/279 R |
| 3,740,403 | 6/1973 | Murdock | 260/279 R |

FOREIGN PATENT DOCUMENTS 251021 7/1948 Switzerland.

OTHER PUBLICATIONS

Marxer, Helv. Chim Acta 49(1) 572–580 (1966), (Chemical Abstract only supplied (CA 64 12669a).
Albert, "The Acridines", 2nd ed. p. 331, N.Y. St. Martins Press (1966).

Primary Examiner—Donald G. Daus
Assistant Examiner—Diana G. Rivers
Attorney, Agent, or Firm—Thomas L. Johnson; B. Woodrow Wyatt

[57] ABSTRACT

9-Phenyl(or benzyl)acridines, 9-phenyl(or benzyl)-9-acridinols and acridinium compounds, useful as trypanosomacidal and antibacterial agents, are prepared from dialkylaminoalkoxy substituted 9-acridinones via reaction with the appropriate Grignard reagents or aryllithium.

10 Claims, No Drawings

AMINOALKOXY SUBSTITUTED 9(ARYL OR ARALKYL)-ACRIDINES

This application is a continuation-in-part of application Ser. No. 677,772, filed April 16, 1976, now abandoned.

BACKGROUND OF THE INVENTION

1. Field of the Invention

This invention relates to certain novel acridine compounds, to the preparation thereof, and to compositions and methods for the use thereof in combatting trypanosomal infections.

2. Description of the Prior Art

Dialkylaminoalkoxy substituted 9(10H)-acridinones, unsubstituted on the nitrogen atom stated to be useful as anthelmintic, antifungal and antitrypanosomal agents, are disclosed in Steiger U.S. Pat. No. 2,732,373 (Jan. 24, 1956).

9-(Alkoxyphenyl)-9-acridinols and 9-(alkoxyphenyl)acridinium salts, stated to be useful as antiseptics, are disclosed in Tabern U.S. Pat. No. 2,645,594 (July 14, 1953).

SUMMARY OF THE INVENTION

In a composition of matter aspect, the invention relates to pharmaceutically acceptable acid-addition salts of compounds of the formula

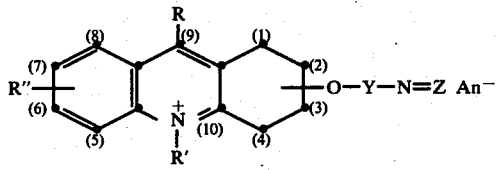

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y— is lower-alkylene of from two to four carbon atoms wherein the terminal valences are on separate carbon atoms; N=Z is di-lower-alkylamino, piperidino, pyrrolidino, morpholino or N-methylpiperazino; and An- is a pharmaceutically acceptable anion.

In a further composition of matter aspect, the invention relates to compounds of the formula

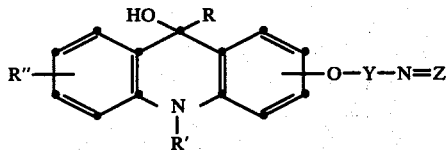

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y— is lower-alkylene of from two to four carbon atoms wherein the terminal valences are on separate carbon atoms; and N=Z is di-lower-alkylamino, piperidino, pyrrolidino, morpholino or N-methylpiperazino; or a lower-alkyl halide or R°-sulfonate quaternary ammonium salt thereof wherein R° is lower-alkyl or aralkyl.

In a further composition of matter aspect, the invention relates to compounds of the formula

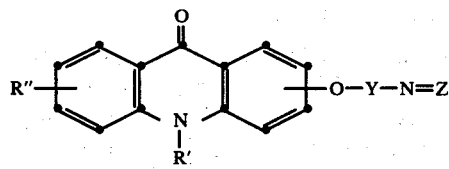

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y— is lower-alkylene of from two to four carbon atoms wherein the terminal valences are on separate carbon atoms; and N=Z is di-lower-alkylamino, piperidino, pyrrolidino, morpholino or N-methylpiperazino; or a pharmaceutically acceptable acid-addition salt thereof; or a lower-alkyl halide or R°-sulfonate quaternary ammonium salt thereof wherein R° is lower-alkyl or aralkyl.

In a further composition of matter aspect, the invention relates to compounds of the formula

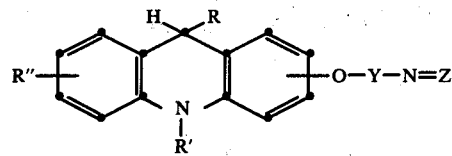

wherein R' is lower-alkyl or benzyl; R" is hydrogen, chloro or lower-alkoxy; —Y— is lower-alkylene of from two to four carbon atoms wherein the terminal valences are on separate carbon atoms; N=Z is di-lower-alkylamino, piperidino, pyrrolidino, morpholino or N-methylpiperazino; or a pharmaceutically acceptable acid-addition salt thereof.

In a further composition of matter aspect, the invention relates to a composition for combatting trypanosomes which comprises a trypanosomacidally effective amount of at least one compound of formula I, II or III in admixture with a suitable carrier or diluent.

In a process aspect, the invention relates to a process for preparing a compound of formula I which comprises treating a compound of formula II with a strong acid.

In a further process aspect, the invention relates to a process for preparing a compound of formula II which comprises reacting a compound of formula IV with RLi or RMg halide.

In a further process aspect, the invention relates to a process for preparing a compound of formula III which comprises reducing a compound of formula I either catalytically or with an alkali metal borohydride or alkali metal aluminum hydride.

In a further process aspect, the invention relates to a process for preparing a compound of formula IV which comprises reacting a compound of the formula

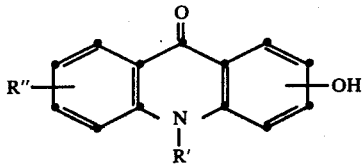

V with a compound of the formula Hal—Y—N=Z, wherein Hal is chlorine or bromine in the presence of a strong base; or reacting a compound of the formula

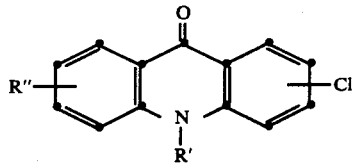

VI wherein R" is hydrogen or lower-alkoxy with a compound of the formula HO—Y—N=Z in the presence of a strong base.

In a further process aspect, the invention relates to a method for combatting a trypanosomal infection in a mammal which comprises administering orally or parenterally to said mammal a trypanosomacidally effective amount of at least one compound of formula I, II or III in admixture with a suitable carrier or diluent.

DETAILED DESCRIPTION INCLUSIVE OF PREFERRED EMBODIMENTS

The compounds of formulas V and VI belong to known classes of compounds, prepared by cyclization of an ortho-arylaminobenzoic acid, followed by N-alkylation. In preparing the compounds of formula V the hydroxy group is protected in the form of the methyl ether which is finally removed by cleavage with hydrobromic acid.

The preparation of a compound of formula IV by reacting a compound of formula V or VI with an amino-alkyl halide (Hal—Y—N=Z) or amino-alkanol (HO—Y—N=Z), respectively, is carried out in the presence of a strong base under essentially anhydrous conditions. The reaction of a compound of formula VI with an amino-alkanol (HO—Y—N=Z) is especially useful in preparing compounds of formula IV where the basic ether side chain is in the 1- or 3-position of the acridine nucleus.

The 9-acridinols of formula II are prepared by reacting a 9-acridinone of formula IV with a compound of the formula RLi or RMg halide. The reaction is carried out in an inert solvent under essentially anhydrous conditions at temperatures ranging from ambient (room) temperature to the reflux temperature of the solvent. The resulting organometallic complex is hydrolyzed with water to give the desired 9-acridinol of formula II.

The 9-acridinols of formula II are readily dehydrated by treatment with a strong acid to give an acridinium salt of formula I where the anion An is that associated with the strong acid used. An acid-addition salt, associated with the terminal amino group of the side chain, is obtained. A preferred method of dehydration comprises treating the acridinol in ethanol containing dissolved hydrogen chloride at a temperature between about 0° C. and the boiling point of the solution (78° C.). This produces an acridinium chloride hydrochloride. Different anions can be obtained by the use of different acids in the dehydration reactions or by conventional ion exchange reactions.

The 9,10-dihydroacridines of formula III are prepared by reduction of the acridinium compounds of formula I. The reduction can be carried out catalytically, for example, with hydrogen in the presence of a platinum or palladium catalyst; or, preferably, by means of a metal hydride such as an alkali metal borohydride or alkali metal aluminum hydride. A preferred metal hydride is sodium borohydride.

The terms "lower-alkyl" or "lower-alkoxy", wherever used in defining the variables, R, R', R" or N=Z, refer to such groups having from one to four carbon atoms which can be straight or branched, preferably primary or secondary alkyl.

The position of the amino-alkoxy side chain can be any of the 1, 2, 3 or 4 positions of the acridine nucleus, the 2 or 3 position being preferred.

The exact nature of the anion An or the acid-addition salt anion is not critical provided it is relatively non-toxic to mammals and thus pharmaceutically acceptable. Such acids include the halides, chloride, bromide and iodide; sulfate, nitrate, phosphate, acetate, lactate, tartrate, cyclohexanesulfamate, tosylate, naphthalenesulfonate, and the like.

A quaternary ammonium salt of a compound of formula II or III is readily formed by interacting a free base of formula II or III with a lower-alkyl halide, for example, methyl iodide; or a lower-alkyl R°-sulfonate, wherein R° is lower-alkyl or aralkyl, such as methyl p-toluenesulfonate, in an inert organic solvent.

Biological evaluation of the compounds of formulas I, II and III has shown that they possess trypanosomacidal activity and antimicrobial properties, and are therefore useful in combatting infections caused by trypanosomal organisms such as *Trypanosoma brucei*, and as antiseptic agents. Certain of the compounds have also demonstrated amebicidal and antiviral activity.

The compounds of formula IV are not only useful as intermediates in preparing the compounds of formulas I, II and III, but are also useful as antiviral agents.

Trypanosomacidal activity was determined against *Trypanosoma brucei* in mice. In a curative test medication was given (orally or parenterally) as a single dose or daily in equally subdivided doses eight hours apart for four days beginning 72 hours after intraperitoneal infection. In a prophylactic-suppressive test the total daily medication was given as a single treatment one day prior to infection, and thereafter for three consecutive days the total daily medications were administered as equally subdivided doses eight hours apart. The infection was uniformly fatal in five to six days in the absence of therapy. Chemotherapeutic effectiveness was based on extension of survival time. Tests were considered terminated 28 days after infection.

The antimicrobial activity of the compounds was determined in vitro by the conventional serial dilution technique against several species of bacteria and fungi, e.g. *S. aureus, S. pyogenes, C. albicans, T. mentagrophytes.*

Amebicidal activity was determined by oral administration of the test compound orally to hamsters infected with *Endameba criceti* and the amount of drug necessary to clear the animals of infection in three days was determined.

Antiviral activity was determined in vitro by the conventional serial dilution technique against selected virus species such as equine rhinovirus and herpes simplex virus I and II.

The compounds can be prepared for use in tablet or capsule form with conventional excipients for oral administration, or in aqueous or oil vehicles for parenteral administration. When used as topical antimicrobial or antiviral agents the compounds can be dissolved in aqueous media and used to disinfect the locus of infection.

The following examples will further illustrate the invention without the latter being limited thereby.

EXAMPLE 1

2-(2-Dimethylaminoethoxy)-10-methyl-9(10H)-acridinone [IV; R' is CH$_3$, R" is H, —O—Y—N=Z is 2—O—CH$_2$CH$_2$N(CH$_3$)$_2$]

To a suspension of 45.0 g. (0.2 m.) of 2-hydroxy-10-methyl-9(10H)-acridinone in 680 ml. of chlorobenzene was added 13.7 g. (0.25 m.) of sodium methoxide and 60 ml. of methanol. The mixture was stirred and heated while distilling off the solvent until the pot temperature reached 130° C. The mixture was allowed to cool to 100° C., 38 g. (0.35 m.) of 2-dimethylaminoethyl chloride was added all at once, and the mixture was stirred at reflux for three hours. After the mixture had cooled to 50° C., 250 ml. of water and 50 ml. of 35% aqueous sodium hydroxide were added and the mixture was stirred for 15 minutes. The organic and aqueous layers were separated and the latter extracted with chloroform. The organic solutions were combined, dried over anhydrous magnesium sulfate and the solvent removed to give a yellow solid which was recrystallized from acetonitrile to give 44.1 g. (74%) of 2-(2-dimethylaminoethoxy)-10-methyl-9(10H)-acridinone, m.p. 115°–117° C.

2-(2-Dimethylaminoethoxy)-10-methyl-9(10H)-acridinone was found to be active in vitro against herpes simplex virus II at a concentration of 3–6 micrograms per milliliter.

EXAMPLE 2 a. 2-Methoxy-10-ethyl-9(10H)-acridinone

To a stirred mixture of 57 g. (0.253 m.) of 2-methoxy-9(10H)-acridinone and 500 ml. of dry dimethylformamide was added in portions 20 g. of 57% sodium hydride in oil (11.4 g., 0.48 m. of NaH). The mixture was stirred for 45 minutes and then 60 ml. (116.4 g., 0.75 m.) of ethyl iodide was added dropwise over a period of 40 minutes. The reaction mixture was stirred for five hours and then poured into water. The resulting solid was collected by filtration, washed with water and recrystallized from ethyl acetate to give 45.1 g. (70%) of 2-methoxy-10-ethyl-9(10H)-acridinone, m.p. 149.5°–152° C.

Similarly, there was prepared, from 3-chloro-9(10H)-acridinone and ethyl acetate, 3-chloro-10-ethyl-9(10H)-acridinone, m.p. 169°–171° C.

b. 2-Hydroxy-10-ethyl-9(10)-acridinone [V; R' is C$_2$H$_5$, R" is H, OH in 2-position]

A mixture of 37.2 g. (0.147 m.) of 2-methoxy-10-ethyl-9(10H)-acridinone and 350 ml. of 48% aqueous hydrogen bromide was stirred at reflux for six hours. The reaction mixture was diluted with water, and the solid product was collected by filtration, washed with water and recrystallized from ethanol to give 27.0 g. (77%) of 2-hydroxy-10-ethyl-9(10H)-acridinone as a yellow solid, m.p. 241°–246° C. (dec.).

c. 2-(2-Dimethylaminoethoxy)-10-ethyl-9(10H)-acridinone [IV; R' is C$_2$H$_5$, R" is H, —O—Y—N=Z is 2—O—CH$_2$CH$_2$N(CH$_3$)$_2$], m.p. 63°–71° C. was prepared in about 50% yield from 2-hydroxy-10-ethyl-9(10H)-acridinone and 2-dimethylaminoethyl chloride according to the method of Example 1. It was also obtained in 78% yield in the form of its hydrochloride salt, m.p. 206°–209° C. (yellow crystals) when recrystallized from an ethanol-ether mixture.

Similarly, employing the appropriate hydroxy-9(10H)-acridinone and aminoalkyl chloride according to Example 1, the following compounds were prepared in yields ranging from 60 to 80 percent.

EXAMPLE 3

2-(3-Dimethylaminopropoxy)-10-methyl-9(10H)-acridinone [IV; R' is CH$_3$, R" is H, —O—Y—N=Z is 2—O—CH$_2$CH$_2$CH$_2$N(CH$_3$)$_2$], m.p. 134°–137° C. (yellow crystals).

EXAMPLE 4

2-(2-Diethylaminoethoxy)-10-methyl-9(10H)-acridinone [IV; R' is CH$_3$, R" is H, —O—Y—N=Z is 2—O—CH$_2$CH$_2$N(C$_2$H$_5$)$_2$], m.p. 97°–100° C.

EXAMPLE 5

2-(2-Dimethylaminoethoxy)-6-chloro-10-methyl-9(10H)-acridinone [IV; R' is CH$_3$, R" is Cl, —O—Y—N=Z is 2—O—CH$_2$CH$_2$N(CH$_3$)$_2$], m.p. 197°–201° C.

EXAMPLE 6

2-(2-Diethylaminoethoxy)-6-chloro-10-methyl-9(10H)-acridinone [IV; R' is CH$_3$, R" is Cl, —O—Y—N=Z is 2—O—CH$_2$CH$_2$N(C$_2$H$_5$)$_2$], m.p. 162°–164.5° C.

EXAMPLE 7

2-[2-(1-Pyrrolidyl)ethoxy]-10-methyl-9(10H)-acridinone [IV; R' is CH$_3$, R" is H, —O—Y—N=Z is 2—O—CH$_2$CH$_2$N(CH$_2$)$_4$], m.p. 154°–159° C. (yellow crystals).

EXAMPLE 8

2-[2-(4-Morpholinyl)ethoxy]-10-methyl-9(10H)-acridinone [IV; R' is CH$_3$, R" is H, —O—Y—N=Z is 2—O—CH$_2$CH$_2$N(CH$_2$)$_4$O], m.p. 146°–149° C. (yellow needles).

EXAMPLE 9

2-[2-(4-Methyl-1-piperazinyl)ethoxy]-10-methyl-9(10H)-acridinone [IV; R' is CH$_3$, R" is H, —O—Y—N=Z is 2—O—CH$_2$CH$_2$N(CH$_2$)$_4$NCH$_3$], m.p. 162°–166° C. (yellow crystals).

EXAMPLE 10

2-[2-(1-Piperidyl)ethoxy]-10-methyl-9(10H)-acridinone [IV; R' is CH$_3$, R" is H, —O—Y—N=Z is 2—O—CH$_2$CH$_2$N(CH$_2$)$_5$], m.p. 125°–127.5° C. (yellow powder).

EXAMPLE 11

2-[2-(1-Pyrrolidyl)ethoxy]-10-ethyl-9(10H)-acridinone [IV; R' is C$_2$H$_5$, R" is H, —O—Y—N=Z is 2—O—CH$_2$CH$_2$N(CH$_2$)$_4$], hydrochloride salt, m.p. 216°–220° C. (yellow powder).

EXAMPLE 12

4-(2-Dimethylaminoethoxy)-10-methyl-9(10H)-acridinone [IV; R' is $CH_3$, R" is H, —O—Y—N=Z is 4—O—$CH_2CH_2N(CH_3)_2$], hydrochloride salt, m.p. 228°–236° C. (tan solid).

EXAMPLE 13

3-(2-Dimethylaminoethoxy)-10-methyl-9-(10H)-acridinone [IV; R' is $CH_3$, R" is H, —O—Y—N=Z is 3—O—$CH_2CH_2N(CH_3)_2$]

A mixture of 48.8 g. (0.2 m.) of 3-chloro-10-methyl-9(10H)-acridinone and 500 ml. of dry dimethylformamide was stirred and heated to 65° C. There was then added all at once 71 g. (0.8 m.) of 2-dimethylaminoethanol, followed by 44.8 g. (0.4 m.) of potassium tertiary-butoxide in portions over a 30 minute period. The reaction mixture was stirred at 60°–65° C. for five hours and then poured into cold water. The solid product was collected, washed with water and recrystallized from acetonitrile to give 54.5 g. (92%) of 3-(2-dimethylaminoethoxy)-10-methyl-9(10H)-acridinone, m.p. 152°–155° C.

Similarly, employing the appropriate chloro-9(10H)-acridinone and amino-alkanol, the following compounds were prepared in 60-80% yield:

EXAMPLE 14

3-(3-Dimethylaminopropoxy)-10-methyl-9(10H)-acridinone [IV; R' is $CH_3$, R" is H, —O—Y—N=Z is 3—O—$CH_2CH_2CH_2N(CH_3)_2$], double m.p. 116.5°–119.5° C.; 127°–129°–129° C., pale green crystals.

EXAMPLE 15

3-[2-(1-Pyrrolidyl)ethoxy]-10-methyl-9(10H)-acridinone [IV; R' is $CH_3$, R" is H, —O—Y—N=Z is 3—O—$CH_2CH_2N(CH_2)_4$], m.p. 117°–120° C., light yellow crystals.

EXAMPLE 16

3-(2-Diethylaminoethoxy)-10-methyl-9(10H)-acridinone [IV; R' is $CH_3$, R" is H, —O—Y—N=Z is 3—O—$CH_2CH_2N(C_2H_5)_2$], m.p. 92.5°–95° C.

EXAMPLE 17

3-(2-Dimethylaminoethoxy)-10-ethyl-9(10H)-acridinone [IV; R' is $C_2H_5$, R" is H, —O—Y—N=Z is 3—O—$CH_2CH_2N(CH_3)_2$], m.p. 114.5°–117° C.

EXAMPLE 18

3-(2-Dimethylaminoethoxy)-7-methoxy-10-methyl-9(10H)-acridinone [IV; R' is $CH_3$, R" is 7—$CH_3O$, —O—Y—N=Z is 3—O—$CH_2CH_2N(CH_2)_2$], m.p. 139°–145° C. (yellow plates).

EXAMPLE 19

3-(2-Diethylaminoethoxy)-7-methoxy-10-methyl-9(10H)-acridinone [IV; R' is $CH_3$, R" is 7—$CH_3O$, —O—Y—N=Z is 3—O—$CH_2CH_2N(C_2H_5)_2$], m.p. 108°–110° C. (pale yellow solid).

EXAMPLE 20

3-(2-Dimethylaminoethoxy)-10-benzyl-9(10H)-acridinone [IV; R' is $C_6H_5CH_2$, R" is H, —O—Y—N=Z is 3—O—$CH_2CH_2N(CH_3)_2$], m.p. 134°–136° C. (light yellow powder). The intermediate 3-chloro-10-benzyl-9(10H)-acridinone, m.p. 186°–190° C. (yellow crystals) was prepared from 3-chloro-9(10H)-acridinone and benzyl bromide with sodium hydride in dimethylformamide.

EXAMPLE 21

1-(2-Dimethylaminoethoxy)-10-methyl-9(10H)-acridinone [IV; R' is $CH_3$, R" is H, —O—Y—N=Z is 1—O—$CH_2CH_2N(CH_3)_2$], hydrochloride salt, m.p. 237°–241° C. (tan granules from methanol-ether). The intermediate 1-chloro-10-methyl-9(10H)-acridinone, m.p. 183°–186° C. (pale yellow granules from ethanol) was prepared by N-methylation of 1-chloro-9(10H)-acridinone, in turn prepared by cyclization of 2-(m-chlorophenylamino)benzoic acid with sulfuric acid.

EXAMPLE 21A 1-(2-Diethylaminoethoxy)-10-methyl-9(10H)-acridinone [IV; R' is $CH_3$, R" is H, —O—Y—N=Z is 1—O—$CH_2CH_2N(C_2H_5)_2$], hydrochloride salt, m.p. 226°–232° C., pale yellow powder.

EXAMPLE 22

1-[2-(1-Pyrrolidinyl)ethoxy]-10-methyl-9(10H)-acridinone [IV; R' is $CH_3$, R" is H, —O—Y—N=Z is 1—O—$CH_2CH_2N(CH_2)_4$], hydrochloride salt, m.p. 221°–225° C. (light yellow powder from ethanol-ether).

EXAMPLE 23

2-(2-Dimethylaminoethoxy)-9,10-dihydro-10-methyl-9-phenyl-9-acridinol [II; R is $C_6H_5$, R' is $CH_3$, R" is H, —O—Y—N=Z is 2—O—$CH_2CH_2N(CH_3)_2$]

To a solution of 17.8 g. (0.06 m.) of 2-(2-dimethylaminoethoxy)-10-methyl-9-(10H)-acridinone (Example 1) in 300 ml. of dry benzene at about 35° C. was added, dropwise, 40 ml. (0.08 m.) of 2M phenyllithium in benzene-ether solution. The reaction mixture was stirred for three hours and allowed to stand overnight. Water (20 ml.) was then added dropwise and the mixture was dried over anhydrous magnesium sulfate. The solvent was removed in vacuo at 45° C. and the residue crystallized from acetonitrile to give 11.2 g. (50%) of 2-(2-dimethylaminoethoxy)9,10-dihydro-10-methyl-9-phenyl-9-acridinol. A second recrystallization from acetonitrile gave a sample with m.p. 157°–161° C.(dec.).

EXAMPLE 24

2-(2-Dimethylaminoethoxy)-9,10-dihydro-10-methyl-9-phenyl-9-acridinol

To a solution of 270 g. (0.8 m.) of 2-(2-dimethylaminoethoxy)-10-methyl-9(10H)-acridinone (Example 1) in 4 liters of dimethylformamide was added 450 ml. of phenylmagnesium bromide (2.9 molar in ether, 1.45 m.) over a one hour period. The reaction mixture was stirred for one hour longer and then added to 22 liters of cold water. The solid product was collected by filtration, slurried with 2 liters of chloroform and filtered. The chloroform filtrate was washed with water, decolorized with activated charcoal and concentrated in vacuo at below 25° C. to a volume of 300 ml. whereupon the solid product separated. The latter was collected, washed with chloroform and n-hexane and dried in vacuo at 25° C. overnight and two hours at 35° C. to give 186 g. (62%) of 2-(2-dimethylaminoethoxy)-9,10-dihydro-10-methyl-9-phenyl-9-acridinol in the form of a monohydrate, m.p. 162°–164° C. (dec.). An additional 21 g. (7%), m.p. 156°–159° C. was obtained from the mother liquors.

2-(2-Dimethylaminoethoxy)-9,10-dihydro-10-methyl-9-phenyl-9-acridinol (15.7 g.) and 25 g. of methyl p-toluenesulfonate in 500 ml. of tetrahydrofuran was held at room temperature for six hours. The mixture was cooled, and the solid product was collected and recrystallized from acetonitrile to give 16.1 g. (71%) of the methyl p-toluenesulfonate quaternary ammonium salt of 2-(2-dimethylaminoethoxy)-9,10-dihydro-10-methyl-9-phenyl-9-acridinol, beige powder, m.p. 109°–114° C.

2-(2-Dimethylaminoethoxy)-9,10-dihydro-10-methyl-9-phenyl-9-acridinol was completely effective orally in the curative test against a murine infection with *Trypanosoma brucei* at a dose level of 25 mg per kg per day for four days; and was completely effective orally in the prophylactic test at a dose level of 50 mg per kg per day. The compound was also completely effective when administered intraperitoneally, subcutaneously or intramuscularly as a single dose of 200 mg/kg three days after infection of the mice.

In a manner similar to the procedure of Example 23 above, employing the appropriate aminoethoxy-10-alkyl-9(10H)acridinone and phenyllithium, there were obtained the following compounds in 40–85% yield:

EXAMPLE 25
2-(2-Diethylaminoethoxy)-9,10-dihydro-10-methyl-9-phenyl-9-acridinol [II; R is $C_6H_5$, R' is $CH_3$, R" is H, —O—Y—N=Z is 2—O—$CH_2CH_2N(C_2H_5)_2$], mottled-purple powder, m.p. 110°–112.5° C. This compound was completely effective orally in the curative test against a murine infection with *T. brucei* at a dose level of 50 mg/kg/day x 4.

EXAMPLE 26
3-(3-Dimethylaminopropoxy)-9,10-dihydro-10-methyl-9-phenyl-9-acridinol [II; R is $C_6H_5$, R' is $CH_3$, R" is H, —O—Y—N=Z is 3—O—$CH_2CH_2CH_2N(CH_3)_2$], pale lavender crystals, m.p. 142°–148° C. (dec.).

EXAMPLE 27
3-(2-Dimethylaminoethoxy)-9,10-dihydro-10-methyl-9-phenyl-9-acridinol [II; R is $C_6H_5$, R' is $CH_3$, R" is H, —O—Y—N=Z is 3—O—$CH_2CH_2N(CH_3)_2$], pale rose crystals, m.p. 132°–136° C.(dec.).

EXAMPLE 28
3-[2-(1-Pyrrolidyl)ethoxy]-9,10-dihydro-10-methyl-9-phenyl-9-acridinol [II; R is $C_6H_5$, R' is $CH_3$, R" is H, —O—Y—N=Z is 3—O—$CH_2CH_2N(CH_2)_4$], m.p. 154°–158° C., salmon colored crystals.

EXAMPLE 29
3-(2-Diethylaminoethoxy)-9,10-dihydro-10-methyl-9-phenyl-9-acridinol [II; R is $C_6H_5$, R' is $CH_3$, R" is H, —O—Y—N=Z is 3—O—$CH_2CH_2N(C_2H_5)_2$], m.p. 145°–148° C., pale orange crystals.

EXAMPLE 30
2-(2-Dimethylaminoethoxy)-6-chloro-9,10-dihydro-10-methyl-9-phenyl-9-acridinol [II; R is $C_6H_5$, R' is $CH_3$, R" is Cl, —O—Y—N=Z is 2—O—$CH_2N(CH_3)_2$], m.p. 161°–164° C., rose crystals.

EXAMPLE 31
2-(2-Diethylaminoethoxy)-6-chloro-9,10-dihydro-10-methyl-9-phenyl-9-acridinol [II; R is $C_6H_5$, R' is $CH_3$, R" is Cl, —O—Y—N=Z is 2—O—$CH_2CH_2N(C_2H_5)_2$], m.p. 105°–108° C., pale pink powder.

EXAMPLE 32
3-(2-Dimethylaminoethoxy)-10-benzyl-9,10-dihydro-9-phenyl-9-acridinol [II; R is $C_6H_5$, R' is $CH_2C_6H_5$, R" is H, —O—Y—N=Z is 3—O—$CH_2CH_2N(CH_3)_2$], m.p. 97°–103° C., light pink powder.

EXAMPLE 33
3-(2-Dimethylaminoethoxy)-10-ethyl-9,10-dihydro-9-phenyl-9-acridinol [II; R is $C_6H_5$, R' is $C_2H_5$, R" is H, —O—Y—N=Z is 3—O—$CH_2CH_2N(CH_3)_2$], m.p. 166°–170° C.(dec.), salmon needles.

EXAMPLE 34
3-[2-(4-Morpholinyl)ethoxy]-10-methyl-9,10-dihydro-9-phenyl-9-acridinol [II; R is $C_6H_5$, R' is $CH_3$, R" is H, —O—Y—N=Z is 3—O—$CH_2CH_2N(CH_2)_4O$], m.p. 158°–161° C.(dec.), white needles.

EXAMPLE 35
2-[2-(1-Pyrrolidyl)ethoxy]-10-methyl-9,10-dihydro-9-phenyl-9-acridinol [II; R is $C_6H_5$, R' is $CH_3$, R" is H, —O—Y—N=Z is 2—O—$CH_2CH_2N(CH_2)_4$], m.p. 145°–148° C., pale green crystals.

EXAMPLE 36
2-(3-Dimethylaminopropoxy)-10-methyl-9,10-dihydro-9-phenyl-9-acridinol [II; R is $CH_3$, R" is H, —O—Y—N=Z is 2—O—$CH_2CH_2CH_2N(CH_3)_2$], m.p. 155°–159° C., off-white solid.

EXAMPLE 37
2-[2-(4-Morpholinyl)ethoxy]-10-methyl-9,10-dihydro-9-phenyl-9-acridinol [II; R is $C_6H_5$, R' is $CH_3$, R" is H, —O—Y—N=Z is 2—O—$CH_2CH_2N(CH_2)_4O$], m.p. 150°–155° C.(dec.), grey solid.

EXAMPLE 38
2-(3-Diethylaminopropoxy)-10-methyl-9,10-dihydro-9-phenyl-9-acridinol [II; R is $C_6H_5$, R' is $CH_3$, R" is H, —O—Y—N=Z is 2—O—$CH_2CH_2CH_2N(C_2H_5)_2$], m.p. 114°–118° C.(dec.), tan crystals.

EXAMPLE 39
2-(2-Dimethylaminoethoxy)-10-ethyl-9,10-dihydro-9-phenyl-9-acridinol [II; R is $C_6H_5$, R' is $C_2H_5$, R" is H, —O—Y—N=Z is 2—O—$CH_2CH_2N(CH_3)_2$], m.p. 156°–161° C.(dec.), pale green powder.

EXAMPLE 40
2-[2-(1-Piperidyl)ethoxy]-10-methyl-9,10-dihydro-9-phenyl-9-acridinol [II; R is $C_6H_5$, R' is $CH_3$, R" is H, —O—Y—N=Z is 2—O—$CH_2CH_2N(CH_2)_5$], m.p. 145°–149° C.(dec.), off-white granules.

EXAMPLE 41
1-(2-Dimethylaminoethoxy)-10-methyl-9,10-dihydro-9-phenyl-9-acridinol [II; R is $C_6H_5$, R' is $CH_3$, R" is H, —O—Y—N=Z is 1—O—$CH_2CH_2N(CH_3)_2$], m.p. 168°–173° C.(dec.), pale green crystals.

EXAMPLE 42
2-[2-(4-Methyl-1-piperazinyl)ethoxy]-10-methyl-9,10-dihydro-9-phenyl-9-acridinol [II; R is $C_6H_5$, R' is $CH_3$, R" is H, —O—Y—N=Z is 2—O—$CH_2CH_2N(CH_2)_4NCH_3$], not purified but converted directly to acridinium compound of Example 50 below.

EXAMPLE 43

4-(2-Dimethylaminoethoxy)-10-methyl-9,10-dihydro-9-phenyl-9-acridinol [II; R is $C_6H_5$, R' is $CH_3$, R" is H, —O—Y—N=Z is 4—O—$CH_2CH_2N(CH_3)_2$], m.p. 147°-151° C., light violet solid.

EXAMPLE 44

2-(2-Dimethylaminoethoxy)-9,10-dihydro-9-(4-methoxyphenyl)-10-methyl-9-acridinol [II; R is 4-$CH_3OC_6H_4$, R' is $CH_3$, R" is H, —O—Y—N=Z is 2—O—$CH_2CH_2N(CH_3)_2$]

4-Methoxyphenylmagnesium bromide (33 ml. of 1.4M in tetrahydrofuran, 0.04 m.) was added, dropwise, to a solution of 11.84 g. (0.04 m.) of 2-(2-dimethylaminoethoxy)-10-methyl-9(10H)-acridinone (Example 1) in 200 ml. of benzene. The reaction mixture was stirred for 5.5 hours at room temperature and allowed to stand overnight. Water (15 ml.) was then added, the mixture filtered and the filtrate dried over anhydrous magnesium sulfate. The solvent was removed in vacuo at 50° C. and the residue crystallized from acetonitrile to give 6.4 g. (40%) of 2-(2-dimethylaminoethoxy)-9,10-dihydro-9-(4-methoxyphenyl)-10-methyl-9-acridinol. A sample when recrystallized from acetonitrile had the m.p. 144°-149° C.(dec.) (pale pink powder).

2-(2-Dimethylaminoethoxy)-9,10-dihydro-9-(4-methoxyphenyl)-10-methyl-9-acridinol was completely effective orally in the curative test against a murine infection with *T. brucei* at a dose level of 200 mg/kg/day × 4.

EXAMPLE 45

2-(2-Dimethylaminoethoxy)-10-methyl-9-phenylacridinium chloride hydrochloride [I; R is $C_6H_5$, R' is $CH_3$, R" is H, —O—Y—N=Z is 2—O—$CH_2CH_2N(CH_3)_2$, An is Cl]

To a solution prepared from 2.62 g. (0.007 m.) of 2-(2-dimethylaminoethoxy)-9,10-dihydro-10-methyl-9-phenyl-9-acridinol (Example 23) and 125 ml. of boiling absolute ethanol was added 3 ml. (0.02 m.) of 7N ethanolic hydrogen chloride. The solution was then diluted with 325 ml. of absolute ether and cooled. The solid product which separated was collected, washed with acetone and dried at 90° C. to give 2.7 g. (86%) of 2-(2-dimethylaminoethoxy)-10-methyl-9-phenylacridinium chloride hydrochloride in the form of a monohydrate, orange needles, m.p. 194°-197° C.(dec.).

In another run 120 g. of the 9-acridinol was slurried in 1050 ml. of absolute ethanol and 60 ml. of concentrated aqueous hydrochloric acid was added over a two minute period. The mixture was stirred for 85 minutes and the product isolated by diluting the solution with ether while seedling with a sample of the desired product. There was obtained 91 g. (61%) of 2-(2-dimethylaminoethoxy)-10-methyl-9-phenylacridinium chloride hydrochloride in the form of a monohydrate, m.p. 215°-218° C.

2-(2-Dimethylaminoethoxy)-10-methyl-9-phenylacridinium chloride was completely effective orally in the curative test against a murine infection with *T. brucei* at a dose level of 25 mg/kg/day × 4. The compound was toxic upon parenteral administration but showed some curative effect at the 50 mg/kg dose level.

EXAMPLE 46

2-(2-Dimethylaminoethoxy)-10-methyl-9-phenylacridinium chloride hydrochloride

A solution containing 0.23 moles of phenylmagnesium bromide was prepared by diluting 78 ml. of 3.0M phenylmagnesium bromide in ether with 200 ml. of dry tetrahydrofuran. This solution was added to a thin slurry of 46.0 g. (0.155 m.) of 2-(2-dimethylaminoethoxy)-10-methyl-9(10H)-acridinone (Example 1) in 460 ml. of tetrahydrofuran over a 2.5 hr. period. The internal temperature stayed below 32° C. during this addition. After 16 hrs. of stirring, 15 ml. of water was cautiously added to the reaction mixture and the solvent was removed under reduced pressure. The mushy residue was slurried with 300 ml. of chloroform and filtered. The filtrate was washed once with 200 ml. of water, dried over sodium sulfate and the chloroform was removed in vacuo to leave 66 g. of dark residue. This residue was slurried in 165 ml. of ethanol, treated with 33.4 ml. (0.4 m.) of concentrated hydrochloric acid and then stirred for 30 min. at room temperature. The dark solution was diluted with 250 ml. of ether and then it was stirred as a heavy yellow precipitate formed. After chilling in an ice bath, the product was collected and dried overnight in vacuo at 60° C. to give 52.0 g. (75%), 2-(2-dimethylaminoethoxy)-10-methyl-9-phenylacridinium chloride hydrochloride in the form of a monohydrate, m.p. 200°-202° C., identical with the compound obtained in Example 45.

By procedures similar to that used in Example 45, employing the appropriate 9-acridinol compound, the following compounds were prepared:

EXAMPLE 47

3-(3-Dimethylaminopropoxy)-10-methyl-9-(4-methoxyphenyl)acridinium chloride hydrochloride [I; R is 4-$CH_3OC_6H_4$, R' is $CH_3$, R" is H, —O—Y—N=Z is 3—O—$CH_2CH_2CH_2N(CH_3)_2$, An is Cl], monohydrate, orange powder, m.p. 162°-168° C.(dec.).

EXAMPLE 48

3-(2-Dimethylaminoethoxy)-10-methyl-9-phenylacridinium chloride hydrochloride [I; R is $C_6H_5$, R' is $CH_3$, R" is H, —O—Y'N=Z is 3—O—$CH_2CH_2N(CH_3)_2$, An is Cl], monohydrate, m.p. 157°-163° C.(dec.).

EXAMPLE 49

2-[2-(4-Morpholinyl)ethoxy]-10-methyl-9-phenylacridinium chloride hydrochloride [I; R is $C_6H_5$, R' is $CH_3$, R" is H, —O—Y—N=Z is 2—O—$CH_2CH_2N(CH_2)_4O$, An is Cl], hemihydrate ethanolate, m.p. 172°-177° C.(dec.) (yellow granules from ethanol-ether).

EXAMPLE 50

2-[2-(1-Pyrrolidyl)ethoxy]-10-methyl-9-phenylacridinium chloride hydrochloride [I; R is $C_6H_5$, R' is $CH_3$, R" is H, —O—Y—N=Z is 2—O—$CH_2CH_2N(CH_2)_4$, An is Cl], monohydrate, m.p. 192°-194° C.(dec.) (yellow plates).

EXAMPLE 51

2-[2-(4-Methyl-1-piperazinyl)ethoxy]-10-methyl-9-phenylacridinium chloride dihydrochloride [I; R is $C_6H_5$, R' is $CH_3$, R" is H, —O—Y—N=Z is 2—O—CH$_2$CH$_2$N(CH$_2$)$_4$NCH$_3$, An is Cl], monohydrate, mp. 215°–225° C.(dec.), orange powder.

EXAMPLE 52

2-[2-(1-Piperidyl)ethoxy]-10-methyl-9-phenylacridinium chloride hydrochloride [I; R is C$_6$H$_5$, R' is CH$_3$, R" is H, —O—Y—N=Z is 2—O—CH$_2$CH$_2$N(CH$_2$)$_5$, An is Cl], hydrate, m.p. 198°–201° C.(dec.), yellow crystals.

EXAMPLE 53

1-(2-Dimethylaminoethoxy)-10-methyl-9-phenylacridinium chloride trihydrochloride [I; R is C$_6$H$_5$, R' is CH$_3$, R" is H, —O—Y—N=Z is 1—O—CH$_2$CH$_2$N(CH$_3$)$_2$, An is Cl], m.p. 222°–225° C., reddish-orange crystals.

According to the procedure described above in Example 44, it is contemplated that each of 2-(2-dimethylaminoethoxy)-9,10-dihydro-10-ethyl-9-phenyl-9-acridinol and 4-(2-dimethylaminoethoxy)-9,10-dihydro-10-methyl-9-phenyl-9-acridinol can be dehydrated with hydrochloric acid to produce the hydrochloride of 2-(2-dimethylaminoethoxy)-10-ethyl-9-phenylacridinium chloride and 4-(2-dimethylaminoethoxy)-10-methyl-9-phenylacridinium chloride, respectively.

EXAMPLE 54

2-(2-Dimethylaminoethoxy)-10-methyl-9-benzylacridinium chloride hydrochloride [I; R is CH$_2$C$_6$H$_5$, R' is CH$_3$, R" is H, —O—Y—N=Z is 2—O—CH$_2$CH$_2$N(CH$_3$)$_2$, An is Cl]

To the Grignard reagent prepared from magnesium and 19.2 g. (0.151 m.) of benzyl chloride in 200 ml. of absolute ether was added, dropwise with stirring, 14.24 g. (0.048 m.) of 2-(2-dimethylaminoethoxy)-10-methyl-9(10H)-acridinone (Example 1) in 300 ml. of benzene. The reaction mixture was heated at reflux for ten hours. Water was then added dropwise until the organometallic complex was hydrolyzed, and the mixture was filtered. The filtrate was dried over anhydrous magnesium sulfate and the solvent removed in vacuo. The residue comprising 2-(2-dimethylaminoethoxy)-9,10-dihydro-10-methyl-9-benzyl-9-acridinol [II; R is CH$_2$C$_6$H$_5$, R' is CH$_3$, R" is H, —O—Y—N=Z is 2—O—CH$_2$CH$_2$N(CH$_3$)$_2$] was warmed with excess ethanolic hydrogen chloride. The solid which formed upon cooling the mixture was collected and recrystallized from an ethanol-ether mixture to give 11.9 g. of 2-(2-dimethylaminoethoxy)-10-methyl-9-benzylacridinium chloride hydrochloride in the form of a dihydrate. A sample when recrystallized from ethanol-ether had the m.p. 216°–218° C. (orange needles).

2-(2-Dimethylaminoethoxy)-10-methyl-9-benzylacridinium chloride was completely effective orally in the curative test against a murine infection with T. brucei at a dose level of 100 mg/kg/day × 4. It was also active orally against Endameba criceti in hamsters at 100 mg/kg.

By procedures similar to that used in Example 54, employing the appropriate 9-acridinone compound, and proceeding through the intermediate 9-benzyl-9-acridinol compound without isolation thereof, the following compounds were prepared:

EXAMPLE 55

2-(2-Dimethylaminoethoxy)-10-methyl-9-(4-fluorobenzyl)acridinium chloride hydrochloride [I; R is CH$_2$C$_6$H$_4$F-4, R' is CH$_3$, R" is H, —O—Y—N=Z is 2—O—CH$_2$CH$_2$N(CH$_3$)$_2$, An is Cl], hydrate (1.5 H$_2$O), orange needles, m.p. 182°–185° C. This compound was completely effective orally in the curative test against a murine infection with T. brucei at a dose level of 200 mg/kg/day × 4. It was also active orally against Endameba criceti in hamsters at 100 mg/kg.

EXAMPLE 56

2-(2-Dimethylaminoethoxy)-10-methyl-9-(4-methylbenzyl)acridinium chloride hydrochloride [I; R is CH$_2$C$_6$H$_4$CH$_3$, R' is CH$_3$, R" is H, —O—Y—N=Z is 2—O—CH$_2$CH$_2$N(CH$_3$)$_2$, An is Cl], hydrate (1.5 H$_2$O), yellow powder, m.p. 170°–178° C.(dec.). This compound was ineffective orally in the curative test against a murine infection with T. brucei at a dose level of 200 mg/kg/day × 4, but showed bacteriostatic activity against S. aureus and S. pyogenes, minimum inhibitory concentration (MIC) 15.6 μg/ml and 7.8 μg/ml, respectively.

EXAMPLE 57

3-(2-Dimethylaminoethoxy)-10-methyl-9-benzylacridinium chloride hydrochloride [I; R is CH$_2$C$_6$H$_5$, R' is CH$_3$, R" is H, —O—Y—N=Z is 3—O—CH$_2$CH$_2$N(CH$_3$)$_2$, An is Cl], dihydrate, orange powder, m.p. 170°–178° C.(dec.). This compound was completely effective orally in the curative test against a murine infection with T. brucei at a dose level of 100 mg/kg.day × 4; and showed bacteriostatic activity against S. aureus and S. pyogenes at MIC 31.3 μg/ml.

EXAMPLE 58

3-(3-Dimethylaminopropoxy)-10-methyl-9-benzylacridinium chloride hydrochloride [I; R is CH$_2$C$_6$H$_5$, R' is CH$_3$, R" is H, —O—Y—N=Z is 3—O—CH$_2$CH$_2$CH$_2$N(CH$_3$)$_2$, An is Cl], dihydrate, orange powder, m.p. 168°–173° C.(dec.). This compound was completely effective orally in the curative test against a murine infection with T. brucei at a dose level of 100 mg/kg/day × 4; and showed bacteriostatic activity against S. aureus at MIC 31.3 μg/ml.

EXAMPLE 59

2-(2-Dimethylaminoethoxy)-10-methyl-9-(4-chlorobenzyl)acridinium chloride hydrochloride [I; R is CH$_2$C$_6$H$_4$Cl-4, R' is CH$_3$, R" is H, —O—Y—N=Z is 2—O—CH$_2$CH$_2$N(CH$_3$)$_2$, An is Cl], hydrate (1.5 H$_2$O), orange solid, m.p. 170°–175° C.(dec.). This compound was ineffective orally in the curative test against a murine infection with T. brucei at a dose level of 200 mg/kg/day × 4, but showed bacteriostatic activity against S. aureus at MIC 7.8 μg/ml, and antiviral activity against herpes II at 25 μg/ml.

EXAMPLE 60

2-(2-Dimethylaminoethoxy)-10-methyl -9-(3-fluorobenzyl)acridinium chloride hydrochloride [I; R is CH$_2$C$_6$H$_4$F-3, R' is CH$_3$, R" is H, —O—Y—N=Z is 2—O—CH$_2$CH$_2$N(CH$_3$)$_2$, An is Cl], dihydrate, light brown powder, m.p. 207°–211° C.(dec.). This compound was completely effective orally in the curative test against a murine infection with T. brucei at a dose level of 200 mg/kg/day × 4; and showed bacteriostatic activity against S. aureus and S. pyogenes at MIC 15.6 μg/ml.

EXAMPLE 61

2-(2-Diethylaminoethoxy)-10-methyl-9-benzylacridinium chloride hydrochloride [I; R is $CH_2C_6H_5$, R' is $CH_3$, R" is H, —O—Y—N=Z is 2—O—$CH_2CH_2N(C_2H_5)_2$, An is Cl], monohydrate, yellow powder, m.p. 103°–107° C. This compound was completely effective orally in the curative test against a murine infection with *T. brucei* at a dose level of 100 mg/kg/day × 4; and showed bacteriostatic activity against *S. aureus* and *S. pyogenes* at MIC 31.3 μg/ml.

EXAMPLE 62

2-(2-Dimethylaminoethoxy)-6-chloro-10-methyl-9-benzylacridinium chloride hydrochloride [I; R is $CH_2C_6H_5$, R' is $CH_3$, R" is 6-Cl, —O—Y—N=Z is 2—O—$CH_2CH_2N(CH_3)_2$, An is Cl], monohydrate, orange crystals, m.p. 200°–208° C.(dec.). This compound in the oral curative test against a murine infection with *T. brucei* was toxic to the animals at 200 mg/kg/day × 4 and ineffective at 50 mg/kg/day × 4. It showed bacteriostatic and fungistatic activity against *S. pyogenes*, *C. albicans* and *T. mentagrophytes* at MIC 7.8 μg/ml, 15.6 μg/ml and 31.3 μg/ml, respectively; and had antiviral activity against herpes II at 12 μg/ml.

EXAMPLE 63

3-(2-Dimethylaminoethoxy)-7-methoxy-10-methyl-9-benzylacridinium chloride hydrochloride [I; R is $CH_2C_6H_5$, R' is $CH_3$, R" is 7-$CH_3O$, —O—Y—N=Z is 3—O—$CH_2CH_2N(CH_3)_2$, An is Cl], hydrate, m.p. 180°–183° C.(dec.), orange crystals. This compound was ineffective against *T. brucei* at a dose level of 200 mg/kg/day × 4 but showed antiviral activity in vitro against herpes simplex virus II at a concentration of 12 micrograms per milliliter.

EXAMPLE 65

3-(2-Diethylaminoethoxy)-7-methoxy-10-methyl-9-benzylacridinium chloride hydrochloride [I; R is $CH_2C_6H_5$, R' is $CH_3$, R" is 7-$CH_3O$, —O—Y—N=Z is 3—O—$CH_2CH_2N(C_2H_5)_2$, An is Cl], hydrate, m.p. 196°–200° C.(dec.), orange powder.

EXAMPLE 65

2-(2-Dimethylaminoethoxy)-10-methyl-9,10-dihydro-9-phenylacridine [III; R is $C_6H_5$, R' is $CH_3$, R" is H, —O—Y—N=Z is 2—O—$CH_2CH_2N(CH_3)_2$]

A solution of 51.0 g. (0.114 m.) of 2-(2-dimethylaminoethoxy)-10-methyl-9-phenylacridinium chloride hydrochloride (Example 45) in 510 ml. of ethanol was treated with 10.5 g. (0.275 m.) of sodium borohydride in portions over 45 min. The internal temperature was maintained between 10° C. and 15° C. during the addition. The reaction was stirred for 2 hrs. without cooling as the color changed from red to brown to pale yellow. The ethanol was removed under reduced pressure (low heat) and the residue was partitioned between 250 ml. of benzene and 250 ml. of water. The water was extracted 1 × 100 ml. with benzene and the combined organic extracts were washed 2 × 100 ml. with water. After drying the solution over anhydrous sodium sulfate, the benzene was removed in vacuo to leave 43 g. of light red oil. The latter was dissolved in 200 ml. of isopropanol, filtered and treated with a solution of 11.7 ml. (0.14 m.) of concentrated hydrochloric acid in 30 ml. of isopropanol. The mixture was stirred until crystallization was well advanced, then it was chilled to 5° C. and the solid was collected. After drying the solid overnight in vacuo at 50° C., there resulted 38.0 g. (81%) of 2-(2-dimethylaminoethoxy)-10-methyl-9,10-dihydro-9-phenylacridine in the form of its hydrochloride salt monohydrate, m.p. 94°–97° C.

A total of 46 g. of hydrate was slurried with 300 ml. of anhydrous acetone at 40° C. and then the mixture was diluted with 150 ml. of ether. After drying the mixture overnight at 45° C. in vacuo, there resulted 38.0 g. (86% recovery or 70% overall) of anhydrous 2-(2-dimethylaminoethoxy)-10-methyl-9,10-dihydro-9-phenylacridine hydrochloride as a pale yellow solid, m.p. 158°–160° C.

2-(2-Dimethylaminoethoxy)-10-methyl-9,10-dihydro-9-phenylacridine hydrochloride was completely effective orally in the curative test against a murine infection with *T. brucei* at a dose level of 12.5 mg/kg/day × 4.

2-(2-Dimethylaminoethoxy)-10-methyl-9,10-dihydro-9-phenylacridine was also prepared by catalytic hydrogenation of 2-(2-dimethylaminoethoxy)-10-methyl-9-phenylacridinium chloride hydrochloride in the presence of platinum catalyst.

By interacting 2-(2-dimethylaminoethoxy)-10-methyl-9,10-dihydro-9-phenylacridine with methyl iodide or methyl p-toluenesulfonate in tetrahydrofuran solution it is contemplated that the methyl iodide or methyl p-toluenesulfonate quaternary ammonium salts of 2-(2-dimethylaminoethoxy)-10-methyl-9,10-dihydro-9-phenylacridine can be prepared.

According to the procedure of Example 65 the following compounds were prepared in 40–60% yield by reduction of the corresponding acridinium compounds:

EXAMPLE 66

2-[2-(4-Morpholinyl)ethoxy]-10-methyl-9,10-dihydro-9-phenylacridine [III; R is $C_6H_5$, R' is $CH_3$, R" is H, —O—Y—N=Z is 2—O—$CH_2CH_2N(CH_2)_4O$], free base, m.p. 104°–108° C., pale yellow needles from ether.

EXAMPLE 67

2-[2-(1-Pyrrolidyl)ethoxy]-10-methyl-9,10-dihydro-9-phenylacridine [III; R is $C_6H_5$, R' is $CH_3$, R" is H, —O—Y—N=Z is 2—O—$CH_2CH_2N(CH_2)_4$], hydrochloride salt, m.p. 131°–136° C., greenish-tan powder from acetone-ether.

EXAMPLE 68

2-(3-Dimethylaminopropoxy)-10-methyl-9,10-dihydro-9-phenylacridine [III; R is $C_6H_5$, R' is $CH_3$, R" is H, —O—Y—N=Z is 2—O—$CH_2CH_2CH_2N(CH_3)_2$], hydrochloride salt, m.p. 175°–188° C.(dec.), olive-green granules from chloroform-ether.

EXAMPLE 69

2-[2-(1-Piperidyl)ethoxy]-10-methyl-9,10-dihydro-9-phenylacridine [III; R is $C_6H_5$, R' is $CH_3$, R" is H, —O—Y—N=Z is 2—O—$CH_2CH_2N(CH_2)_5$], free base, m.p. 110°–112.5° C., off-white solid from acetonitrile.

EXAMPLE 70

3-(2-Dimethylaminoethoxy)-10-methyl-9,10-dihydro-9-phenylacridine [III; R is $C_6H_5$, R' is $CH_3$, R" is H, —O—Y—N=Z is 3—O—$CH_2CH_2N(CH_3)_2$], hydrochloride, m.p. 100°–106° C. (from ethanol-ether).

EXAMPLE 71

1-(2-Dimethylaminoethoxy)-10-methyl-9,10-dihydro-9-phenylacridine [III; R is C₆H₅, R' is CH₃, R" is H, —O—Y—N=Z is 1—O—CH₂CH₂N(CH₃)₂], m.p. 105°-108° C. (from ethanol).

According to the procedure described above in Example 65 it is contemplated that each of 2-[2-(4-methyl-1-piperazinyl)ethoxy]-10-methyl-9-phenylacridinium chloride dihydrochloride, 2-(2-dimethylaminoethoxy)-10-methyl-9-benzylacridinium chloride hydrochloride, 2-(2-dimethylaminoethoxy)-6-chloro-10-methyl-9-benzylacridinium chloride hydrochloride, 3-(2-dimethylaminoethoxy)-7-methoxy-10-methyl-9-benzylacridinium chloride hydrochloride, 2-(2-dimethylaminoethoxy)-10-ethyl-9-phenylacridinium chloride hydrochloride, and 4-(2-dimethylaminoethoxy)-10-methyl-9-phenylacridinium chloride hydrochloride can be reduced with sodium borohydride to produce, respectively, 2-[2-(4-methyl-1-piperazinyl)ethoxy]-10-methyl-9,10-dihydro-9-phenylacridine, 2-(2-dimethylaminoethoxy)-10-methyl-9,10-dihydro-9-benzylacridine, 2-(2-dimethylaminoethoxy)-6-chloro-10-methyl-9,10-dihydro-9-benzylacridine, 3-(2-dimethylaminoethoxy)-7-methoxy-10-methyl-9,10-dihydro-9-benzylacridine, 2-(2-dimethylaminoethoxy)-10-ethyl-9,10-dihydro-9-phenylacridine, and 4-(2-dimethylaminoethoxy)-10-methyl-9,10-dihydro-9-phenylacridine.

I claim:

1. A compound of the formula

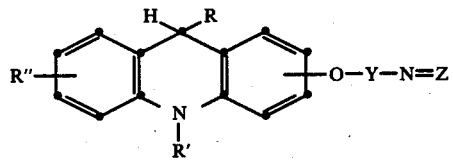

wherein R is phenyl, benzyl, or phenyl or benzyl substituted by a single substituent selected from the group consisting of lower-alkyl, lower-alkoxy or halogen; R' is lower-alkyl or benzyl; R" is hydrogen, chloro or lower-alkoxy; —Y— is lower-alkylene of from two to four carbon atoms wherein the terminal valences are on separate carbon atoms; and N=Z is di-lower-alkylamino, piperidino, pyrrolidino, morpholine or N-methylpiperazino; or a pharmaceutically acceptable acid-addition salt thereof; or a lower-alkyl halide or R°-sulfonate quaternary ammonium salt thereof wherein R° is lower-alkyl or aralkyl.

2. A compound according to claim 1 wherein R is phenyl, R' is methyl and R" is hydrogen.

3. 2-(2-Dimethylaminoethoxy)-9,10-dihydro-10-methyl-9-phenylacridine, according to claim 2.

4. 2-[2-(1-Pyrrolidyl)ethoxy]-9,10-dihydro-10-methyl-9-phenylacridine, according to claim 2.

5. 2-(3-Dimethylaminopropoxy)-9,10-dihydro-10-methyl-9-phenylacridine, according to claim 2.

6. 2-[2-(1-Piperidyl)ethoxy]-9,10-dihydro-10-methyl-9-phenylacridine, according to claim 2.

7. A composition for combatting trypanosomes which comprises a trypanosomacidally effective amount of at least one compound according to claim 1 in admixture with a suitable carrier or diluent.

8. A composition according to claim 7 wherein the compound is 2-(2-dimethylaminoethoxy)-9,10-dihydro-10-methyl-9-phenylacridine.

9. A method for combatting a trypanosomal infection in a mammal which comprises administering orally or parenterally to said mammal a trypanosomacidally effective amount of at least one compound according to claim 1 in admixture with a suitable carrier or diluent.

10. A method according to claim 9 wherein the compound is 2-(2-dimethylaminoethoxy)-9,10-dihydro-10-methyl-9-phenylacridine.

* * * * *

UNITED STATES PATENT AND TRADEMARK OFFICE
CERTIFICATE OF CORRECTION

PATENT NO. : 4,150,134

DATED : April 17, 1979

INVENTOR(S) : John W. Schulenberg

It is certified that error appears in the above-identified patent and that said Letters Patent are hereby corrected as shown below:

Cover page, [75], "Delmar, N.Y." should read --Rensselaer, N.Y.--.

Cover page, [56] References Cited, "U.S. 3,615,416 (10/71) Fox" should be inserted.

Column 1, formula I,

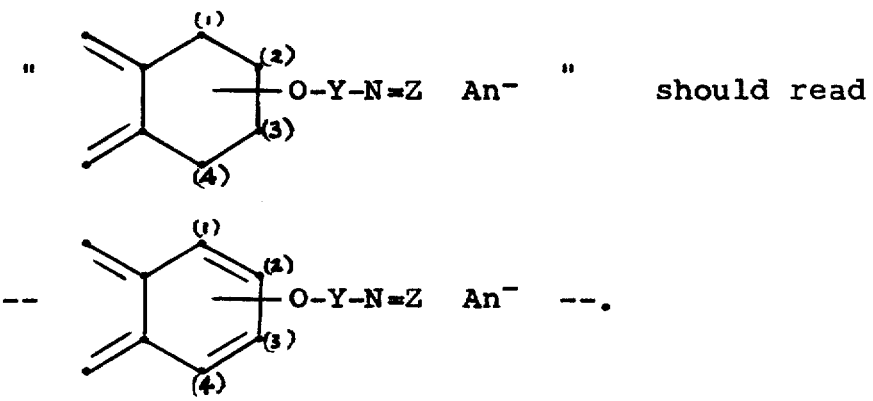

Column 18, line 8, Claim 1, "morpholine" should read --morpholino--.

Signed and Sealed this

Eighteenth Day of March 1980

[SEAL]

Attest:

SIDNEY A. DIAMOND

Attesting Officer    Commissioner of Patents and Trademarks